United States Patent
Raymond et al.

(10) Patent No.: US 9,616,243 B2
(45) Date of Patent: Apr. 11, 2017

(54) DYNAMICALLY ADJUSTABLE MULTIPHASIC DEFIBRILLATOR PULSE SYSTEM AND METHOD

(71) Applicant: CardioThrive, Inc., Concord, CA (US)

(72) Inventors: Douglas M. Raymond, Livermore, CA (US); Peter D. Gray, Vallejo, CA (US); Walter T. Savage, Concord, CA (US); Shelley J. Savage, Concord, CA (US)

(73) Assignee: CardioThrive, Inc., Concord, CA (US)

( * ) Notice: Subject to any disclaimer, the term of this patent is extended or adjusted under 35 U.S.C. 154(b) by 0 days.

(21) Appl. No.: 14/303,541

(22) Filed: Jun. 12, 2014

(65) Prior Publication Data
US 2014/0371805 A1    Dec. 18, 2014

Related U.S. Application Data

(60) Provisional application No. 61/835,443, filed on Jun. 14, 2013.

(51) Int. Cl.
*A61N 1/32* (2006.01)
*A61N 1/39* (2006.01)
*A61N 1/362* (2006.01)

(52) U.S. Cl.
CPC .......... *A61N 1/3912* (2013.01); *A61N 1/3625* (2013.01)

(58) Field of Classification Search
CPC ............ A61N 1/36128; A61N 1/36175; A61N 1/36178; A61N 1/3956; A61N 1/3912; A61N 1/3625
USPC ....... 607/5, 9, 11, 44, 45, 46, 48, 68, 70, 74
See application file for complete search history.

(56) References Cited

U.S. PATENT DOCUMENTS

| | | |
|---|---|---|
| 4,441,498 A | 4/1984 | Nordling |
| 5,199,429 A | 4/1993 | Kroll et al. |
| 5,240,995 A | 8/1993 | Gyory |
| 5,290,585 A | 3/1994 | Elton |
| 5,338,490 A | 8/1994 | Dietz |
| 5,362,420 A | 11/1994 | Itoh |
| 5,402,884 A | 4/1995 | Gilman et al. |
| 5,489,624 A | 2/1996 | Kantner |
| 5,536,768 A | 7/1996 | Kantner |

(Continued)

FOREIGN PATENT DOCUMENTS

| | | |
|---|---|---|
| DE | 10 2006 025864 | 12/2007 |
| EP | 1 834 622 | 9/2007 |

(Continued)

OTHER PUBLICATIONS

Yamanouchi, Yoshio, et al. "Optimal Small-Capacitor Biphasic Waveform for External Defibrillation: Influence of Phase-1 Tilt and Phase-2 Voltage." Jul. 30, 1998. Journal of the American Heart Association. vol. 98. pp. 2487-2493.*

(Continued)

*Primary Examiner* — Christopher D Koharski
*Assistant Examiner* — Michael Carey
(74) *Attorney, Agent, or Firm* — DLA Piper LLP (US)

(57) ABSTRACT

A dynamically adjustable multiphasic pulse system and method are provided. The dynamically adjustable multiphasic pulse system may be used as pulse system for a defibrillator or cardioverter. The dynamically adjustable multiphasic pulse system may generate a positive phase and a negative phase of a pulse to generate a therapeutic pulse.

21 Claims, 8 Drawing Sheets

(56) References Cited

U.S. PATENT DOCUMENTS

| | | | |
|---|---|---|---|
| 5,573,668 A | 11/1996 | Grosh | |
| 5,643,252 A | 7/1997 | Waner et al. | |
| 5,658,316 A | 8/1997 | Lamond et al. | |
| 5,660,178 A | 8/1997 | Kantner | |
| 5,733,310 A | 3/1998 | Lopin et al. | |
| 5,800,685 A | 9/1998 | Perrault | |
| 5,871,505 A | 2/1999 | Adams | |
| 5,987,354 A | 11/1999 | Cooper | |
| 6,006,131 A | 12/1999 | Cooper et al. | |
| 6,056,738 A | 5/2000 | Marchitto et al. | |
| 6,141,584 A | 10/2000 | Rockwell et al. | |
| 6,197,324 B1 | 3/2001 | Crittenden | |
| 6,251,100 B1 | 6/2001 | Flock et al. | |
| 6,256,533 B1 | 7/2001 | Yuzhakov et al. | |
| 6,266,563 B1 | 7/2001 | KenKnight et al. | |
| 6,315,722 B1 | 11/2001 | Yaegashi | |
| 6,329,488 B1 | 12/2001 | Terry | |
| 6,379,324 B1 | 4/2002 | Gartstein et al. | |
| 6,477,413 B1 | 11/2002 | Sullivan et al. | |
| 6,576,712 B2 | 6/2003 | Feldstein | |
| 6,596,401 B1 | 7/2003 | Terry | |
| 6,597,948 B1 | 7/2003 | Rockwell et al. | |
| 6,611,707 B1 | 8/2003 | Prausnitz | |
| 6,690,959 B2 | 2/2004 | Thompson | |
| 6,714,817 B2 | 3/2004 | Daynes et al. | |
| 6,797,276 B1 | 9/2004 | Glenn | |
| 6,803,420 B2 | 10/2004 | Cleary | |
| 6,908,453 B2 | 6/2005 | Fleming | |
| 6,908,681 B2 | 6/2005 | Terry | |
| 6,931,277 B1 | 8/2005 | Yuzhakov | |
| 7,072,712 B2 | 7/2006 | Kroll et al. | |
| 7,108,681 B2 | 9/2006 | Gartstein | |
| 7,226,439 B2 | 6/2007 | Prausnitz | |
| 7,463,917 B2 | 12/2008 | Martinez | |
| 7,645,263 B2 | 1/2010 | Angel et al. | |
| 7,797,044 B2 | 9/2010 | Covey et al. | |
| 8,024,037 B2 | 9/2011 | Kumar | |
| 8,527,044 B2 | 9/2013 | Edwards et al. | |
| 8,558,499 B2 | 10/2013 | Ozaki et al. | |
| 8,781,576 B2 | 7/2014 | Savage et al. | |
| 9,089,718 B2 | 7/2015 | Owen et al. | |
| 2001/0031992 A1 | 10/2001 | Fishler et al. | |
| 2002/0016562 A1 | 2/2002 | Cormier et al. | |
| 2002/0045907 A1 | 4/2002 | Sherman et al. | |
| 2002/0082644 A1 | 6/2002 | Picardo et al. | |
| 2003/0017743 A1 | 1/2003 | Picardo et al. | |
| 2003/0055460 A1 | 3/2003 | Owen et al. | |
| 2003/0088279 A1* | 5/2003 | Rissmann | A61N 1/3931 607/5 |
| 2003/0167075 A1 | 9/2003 | Fincke | |
| 2003/0197487 A1 | 10/2003 | Tamura et al. | |
| 2004/0105834 A1 | 6/2004 | Singh | |
| 2004/0143297 A1 | 7/2004 | Ramsey, III | |
| 2004/0166147 A1 | 8/2004 | Lundy | |
| 2004/0247655 A1 | 12/2004 | Asmus | |
| 2005/0123565 A1 | 6/2005 | Subramony | |
| 2006/0136000 A1 | 6/2006 | Bowers | |
| 2006/0142806 A1 | 6/2006 | Katzman et al. | |
| 2006/0173493 A1 | 8/2006 | Armstrong et al. | |
| 2006/0206152 A1 | 9/2006 | Covey et al. | |
| 2007/0016268 A1 | 1/2007 | Carter et al. | |
| 2007/0078376 A1 | 4/2007 | Smith | |
| 2007/0150008 A1 | 6/2007 | Jones et al. | |
| 2007/0191901 A1 | 8/2007 | Schecter | |
| 2008/0082153 A1 | 4/2008 | Gadsby et al. | |
| 2008/0097546 A1 | 4/2008 | Powers et al. | |
| 2008/0154178 A1 | 6/2008 | Carter et al. | |
| 2008/0177342 A1* | 7/2008 | Snyder | A61N 1/3937 607/8 |
| 2008/0312579 A1 | 12/2008 | Chang et al. | |
| 2008/0312709 A1 | 12/2008 | Volpe et al. | |
| 2009/0076366 A1 | 3/2009 | Palti | |
| 2009/0210022 A1* | 8/2009 | Powers | A61N 1/3906 607/5 |
| 2009/0318988 A1 | 12/2009 | Powers | |
| 2009/0326400 A1 | 12/2009 | Huldt | |
| 2010/0063559 A1 | 3/2010 | McIntyre et al. | |
| 2010/0160712 A1 | 6/2010 | Burnett et al. | |
| 2010/0241181 A1 | 9/2010 | Savage et al. | |
| 2011/0028859 A1 | 2/2011 | Chian | |
| 2011/0071611 A1 | 3/2011 | Khuon et al. | |
| 2011/0208029 A1 | 8/2011 | Joucla et al. | |
| 2011/0237922 A1 | 9/2011 | Parker, III et al. | |
| 2011/0288604 A1 | 11/2011 | Kaib et al. | |
| 2011/0301683 A1 | 12/2011 | Axelgaard | |
| 2012/0101396 A1 | 4/2012 | Solosko et al. | |
| 2012/0112903 A1 | 5/2012 | Kaib et al. | |
| 2012/0136233 A1 | 5/2012 | Yamashita | |
| 2012/0158075 A1 | 6/2012 | Kaib et al. | |
| 2012/0203297 A1 | 8/2012 | Efimov et al. | |
| 2012/0259382 A1 | 10/2012 | Trier et al. | |
| 2014/0005736 A1 | 1/2014 | Geheb | |
| 2014/0221766 A1 | 8/2014 | Kinast | |
| 2014/0277226 A1 | 9/2014 | Poore et al. | |
| 2014/0317914 A1 | 10/2014 | Shaker | |
| 2014/0371566 A1 | 12/2014 | Raymond et al. | |
| 2014/0371567 A1 | 12/2014 | Raymond et al. | |
| 2014/0371805 A1 | 12/2014 | Raymond et al. | |
| 2014/0371806 A1 | 12/2014 | Raymond et al. | |
| 2015/0297104 A1 | 10/2015 | Chen et al. | |
| 2015/0327781 A1 | 11/2015 | Hernandez-Silveira et al. | |

FOREIGN PATENT DOCUMENTS

| | | |
|---|---|---|
| JP | 2005-144164 | 6/2005 |
| JP | 2008302254 | 12/2008 |
| JP | 2012-135457 | 7/2012 |
| JP | 2012-529954 | 11/2012 |
| WO | 03/020362 | 3/2003 |
| WO | WO2010146492 | 12/2010 |

OTHER PUBLICATIONS

Claims of U.S. Appl. No. 14/661,949 as of Mar. 18, 2015.*
PCT International Search Report of PCT/US10/27346; dated Oct. 14, 2010 (4 pgs.).
PCT Written Opinion of the International Searching Authority of PCT/US10/27346; dated Oct. 14, 2010 (7 pgs.).
PCT International Preliminary Report on Patentability of PCT/US12/65712; dated Jun. 10, 2014 (6 pgs.).
PCT International Search Report of PCT/US14/42355; dated Nov. 3, 2010 (2 pgs.).
PCT Written Opinion of the International Searching Authority of PCT/US14/42355; dated Nov. 3, 2014 (6 pgs.).
PCT International Search Report of PCT/US14/42356; dated Nov. 3, 2010 (2 pgs.).
PCT Written Opinion of the International Searching Authority of PCT/US14/42356; dated Nov. 3, 2014 (6 pgs.).
PCT International Search Report of PCT/US14/42360; dated Nov. 4, 2010 (2 pgs.).
PCT Written Opinion of the International Searching Authority of PCT/US14/42360; dated Nov. 4, 2014 (4 pgs.).
PCT International Search Report of PCT/US14/42409; dated Nov. 4, 2010 (2 pgs.).
PCT Written Opinion of the International Searching Authority of PCT/US14/42409; dated Nov. 4, 2014 (4 pgs.).
Chinese First Office Action of CN 201080021650.4 (English and Chinese); dated Jul. 24, 2013 (19 pgs.).
Chinese Second Office Action of CN 201080021650.4 (English and Chinese); dated Jan. 16, 2014 (16 pgs.).
Chinese Third Office Action of CN 201080021650.4 (English and Chinese); dated Jun. 17, 2014 (18 pgs.).
Japanese Notification of Reason for Rejection of JP 2012-500855 (English and Japanese); dated Feb. 17, 2014 (3 pgs.).
PCT International Search Report of PCT/US2012/065712, dated Mar. 29, 2013 (2 pages).
PCT Written Opinion of PCT/US2012/065712, dated Mar. 29, 2013 (5 pages).
PCT International Preliminary Report on Patentability and Written Opinion of PCT/EP2007/009879; dated May 19, 2009 (7 pages).

(56) References Cited

OTHER PUBLICATIONS

PCT International Search Report of PCT/EP2007/009879; dated Apr. 29, 2008 (3 pages).
PCT International Preliminary Report on Patentability of PCT/US2010/027346 dated Sep. 20, 2011 (12 pages).
Extended European Search Report of EP 2408521 dated Jul. 10, 2012 (8 pages).
"Changes in the passive electrical properties of human stratum corneum due electroporation" dated Dec. 7, 1994. By U. Pliquett, R. Langer, and J. C. Weaver (11 pages).
"Electrical properties of the epidermal stratum corneum" dated Aug. 12, 1974. By T. Yamamoto and Y. Yamamoto (8 pages).
"Non-invasive bioimpedance of intact skin: mathematical modeling and experiments" dated May 2, 2010. By U. Birgersson, E. Birgersson, P. Aberg, I. Nicander, and S. Ollmar (19 pages).
"Polymer Microneedles for Controlled-Release Drug Delivery" dated Dec. 2, 2005. By J-H. Park, M. G. Allen, and M. R. Prausnitz (12 pages).
"Utilizing Characteristic Electrical Properties of the Epidermal Skin Layers to Detect Fake Fingers in Biometric Fingerprint Systems—A Pilot Study" dated Dec. 1, 2004. By O. G. Martinsen, S. Clausen, J. B. Nysaether, and S. Grimnes (4 pages).
"Lack of Pain Associated with Microfabricated Microneedles" dated Oct. 10, 2000. By S. Kaushik, A. H. Hord, D. D. Denson, D. V. McAlliser, S. Smitra, M. G. Allen, and M. R. Prausnitz (3 pages).
"Two Dimensional Metallic Microelectrode Arrays for Extracellular Stimulation and Recording of Neurons" dated 1993. By A. B. Frazier, D. P. O'Brien, and M. G. Allen (6 pages).
"Insertion of microneedles into skin: measurement and prediction of insertion force and needle facture force" dated Dec. 10, 2003. By S. P. Davis, B. J. Landis, Z. H. Adams, M. G. Allen, and M. R. Prausnitz (9 pages).
"Microneedle Insertion Force Reduction Using Vibratory Actuation" dated 2004. By M. Yang and J. D. Zahn (6 pages).
Yoshio Yamanouchi, et al., *Optimal Small-Capacitor Biphasic Waveform for External Defibrillation; Influence of Phase-1 Tilt and Phase-2 Voltage* Journal of the American Heart Assocation, vol. 98, pp. 2487-2493 (8 pgs.).

\* cited by examiner figure 1A figure 1B figure 2 figure 3 figure 5 figure 7 figure 6 figure 8 figure 10

DYNAMICALLY ADJUSTABLE MULTIPHASIC DEFIBRILLATOR PULSE SYSTEM AND METHOD

PRIORITY CLAIMS/RELATED APPLICATIONS

This application claims priority to under 35 USC 120 and claims the benefit under 35 USC 119(e) to U.S. Provisional Patent Application Ser. No. 61/835,443 filed Jun. 14, 2013 and titled "Dynamically Adjustable Multiphasic Defibrillator Pulse System and Method", the entirety of which is incorporated herein by reference.

FIELD

The disclosure relates to medical devices and in particular to devices and methods that generate therapeutic treatment pulses used in medical devices, such as cardioverters and defibrillators.

BACKGROUND

A primary task of the heart is to pump oxygenated, nutrient-rich blood throughout the body. Electrical impulses generated by a portion of the heart regulate the pumping cycle. When the electrical impulses follow a regular and consistent pattern, the heart functions normally and the pumping of blood is optimized. When the electrical impulses of the heart are disrupted (i.e., cardiac arrhythmia), this pattern of electrical impulses becomes chaotic or overly rapid, and a sudden cardiac arrest may take place, which inhibits the circulation of blood. As a result, the brain and other critical organs are deprived of nutrients and oxygen. A person experiencing sudden cardiac arrest may suddenly lose consciousness and die shortly thereafter if left untreated.

The most successful therapy for sudden cardiac arrest is prompt and appropriate defibrillation. A defibrillator uses electrical shocks to restore the proper functioning of the heart. A crucial component of the success or failure of defibrillation, however, is time. Ideally, a victim should be defibrillated immediately upon suffering a sudden cardiac arrest, as the victim's chances of survival dwindle rapidly for every minute without treatment.

There are a wide variety of defibrillators. For example, implantable cardioverter-defibrillators (ICD) involve surgically implanting wire coils and a generator device within a person. ICDs are typically for people at high risk for a cardiac arrhythmia. When a cardiac arrhythmia is detected, a current is automatically passed through the heart of the user with little or no intervention by a third party.

Figure 10:
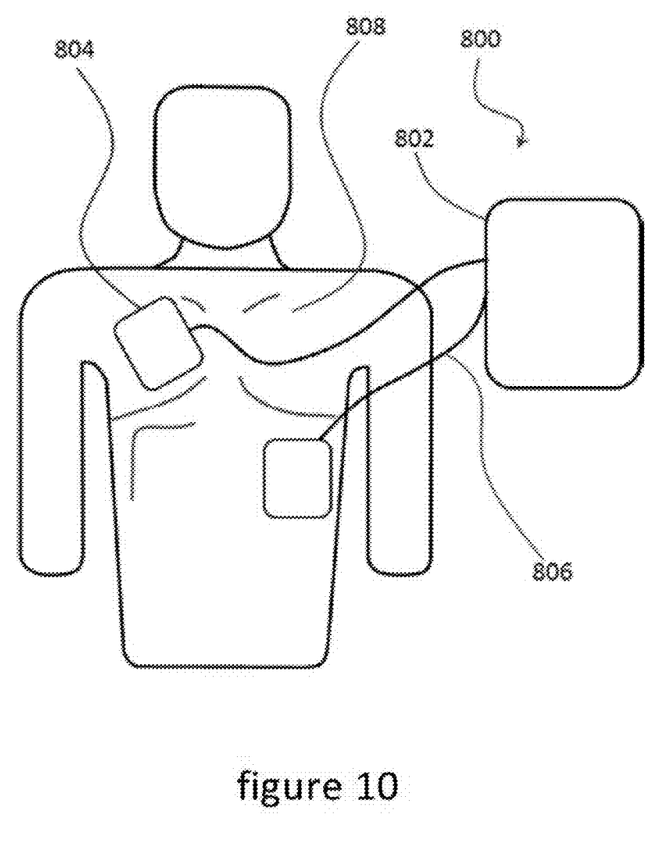
FIG. 10 diagrammatically illustrates an example of a conventional defibrillator.

Another, more common type of defibrillator is the automated external defibrillator (AED). Rather than being implanted, the AED is an external device used by a third party to resuscitate a person who has suffered from sudden cardiac arrest. FIG. 10 illustrates a conventional AED 800, which includes a base unit 802 and two pads 804. Sometimes paddles with handles are used instead of the pads 804. The pads 804 are connected to the base unit 802 using electrical cables 806.

A typical protocol for using the AED 800 is as follows. Initially, the person who has suffered from sudden cardiac arrest is placed on the floor. Clothing is removed to reveal the person's chest 808. The pads 804 are applied to appropriate locations on the chest 808, as illustrated in FIG. 10. The electrical system within the base unit 802 generates a high voltage between the two pads 804, which delivers an electrical shock to the person. Ideally, the shock restores a normal cardiac rhythm. In some cases, multiple shocks are required.

Another type of defibrillator is a Wearable Cardioverter Defibrillator (WCD). Rather than a device being implanted into a person at-risk from Sudden Cardiac Arrest, or being used by a bystander once a person has already collapsed from experiencing a Sudden Cardiac Arrest, the WCD is an external device worn by an at-risk person which continuously monitors their heart rhythm to identify the occurrence of an arrhythmia, to correctly identify the type of arrhythmia involved and then to automatically apply the therapeutic action required for the type of arrhythmia identified, whether the therapeutic action is cardioversion or defibrillation. These devices are most frequently used for patients who have been identified as potentially requiring an ICD and to effectively protect them during the two to six month medical evaluation period before a final decision is made and they are officially cleared for, or denied, an ICD.

The current varieties of defibrillators available on the market today, whether Implantable Cardioverter Defibrillators (ICDs) or Automatic External Defibrillators (AEDs) or any other variety such as Wearable Cardioverter Defibrillators (WCDs), predominantly utilize either a monophasic waveform or a biphasic waveform for the therapeutic defibrillation high-energy pulse. Each manufacturer of defibrillators, for commercial reasons, has their own unique and slightly different take on waveform design for their devices' pulses. Multiple clinical studies over the last couple of decades have indicated that use of a biphasic waveform has greater therapeutic value than a monophasic waveform does to a patient requiring defibrillation therapy and that biphasic waveforms are efficacious at lower levels of energy delivery than monophasic waveforms.

Figure 3:
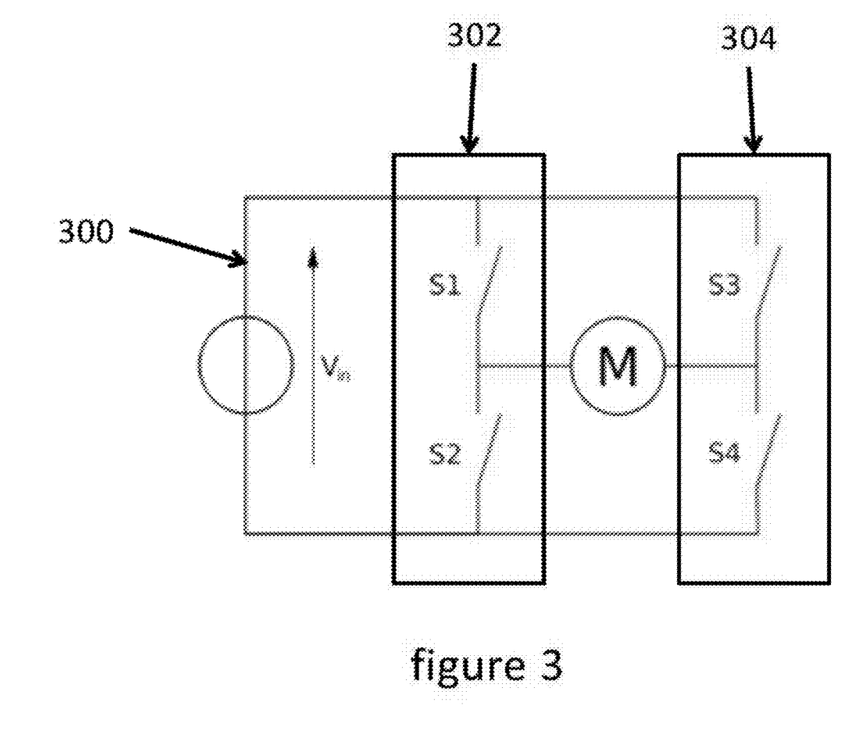
FIG. 3 illustrates a typical H-bridge circuit.

All of the current products that use a biphasic waveform pulse have a single high-energy reservoir, which, while simple and convenient, results in severe limitation on the range of viable pulse shapes that can be delivered. Specifically, the second or Negative phase of the Biphasic waveform is currently characterized by a lower amplitude starting point than the first or Positive phase of the Biphasic waveform, as shown in FIG. 3. This is due to the partial draining of the high-energy reservoir during delivery of the initial Positive phase and then, after inverting the polarity of the waveform so that the Negative phase is able to be delivered, there is only the same partially drained amount of energy remaining in the energy reservoir. This lower amplitude starting point constrains and causes the lower initial amplitude of the Negative phase of the waveform. The typical exponential decay discharge is shown by the Positive phase of the waveform shown in FIG. 5 and how the reservoir would have continued to discharge (if the polarity had not been switched) is shown as a dashed line in FIG. 5.

DETAILED DESCRIPTION OF ONE OR MORE EMBODIMENTS

The disclosure is particularly applicable to a multiphasic pulse system for an external defibrillator and it is in this context that the disclosure will be described. It will be appreciated, however, that the multiphasic pulse system has greater utility since it may be used to generate one or more pulses for other systems. For example, the pulse system may be used to generate therapeutic treatment pulses for other types of defibrillators, cardioverters or other systems. For example, the pulse system may be used to generate therapeutic treatment pulses and then provide the pulses to a patient using paddles or pads. When used for defibrillation, the pulse system may generates the pulses and deliver them to a patient through two defibrillation pads or paddles.

Figure 1A:
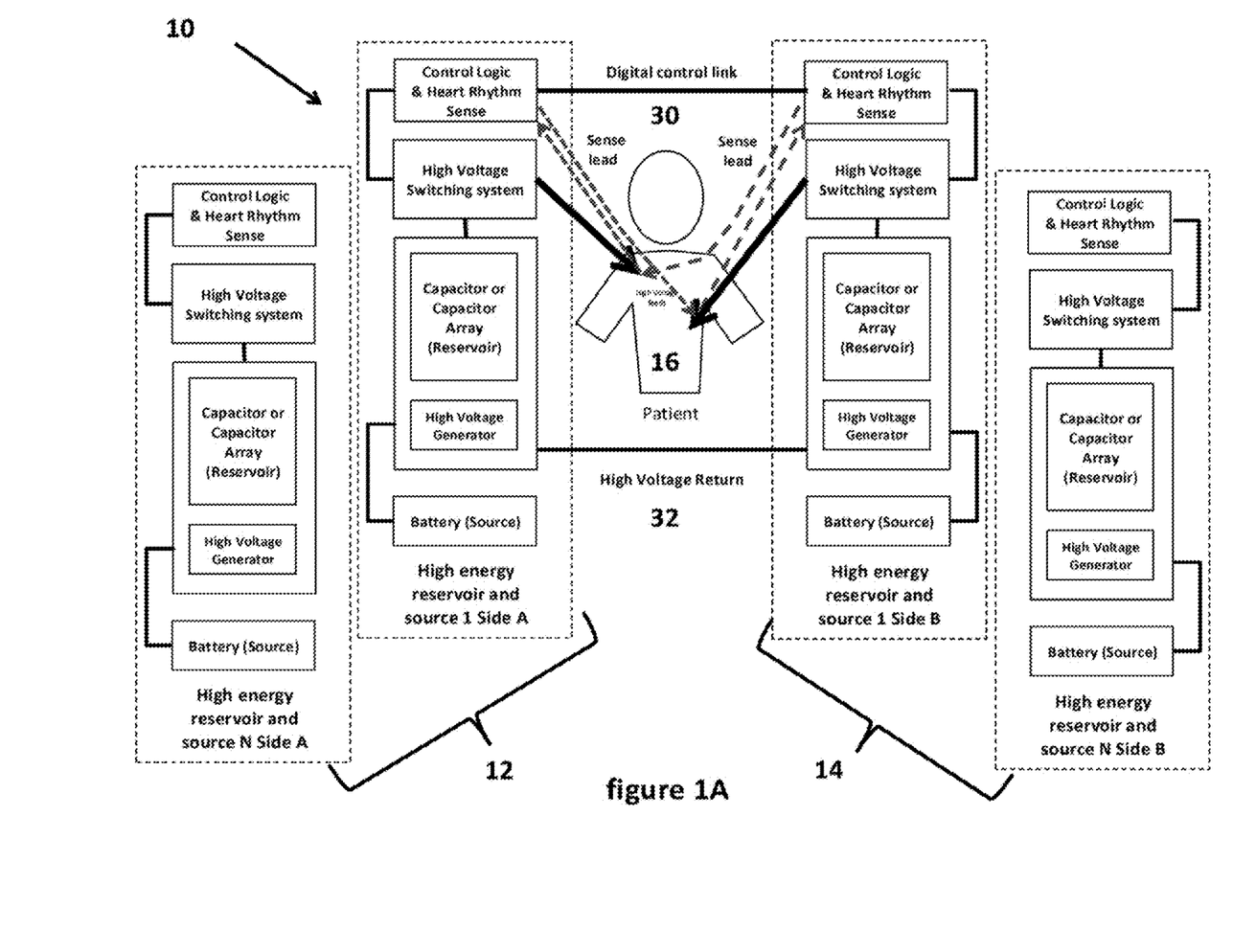
FIGS. 1A and 1B illustrate a multiphasic waveform system with a plurality of independent subsystems each with its own energy reservoir and energy source.
Figure 1B:
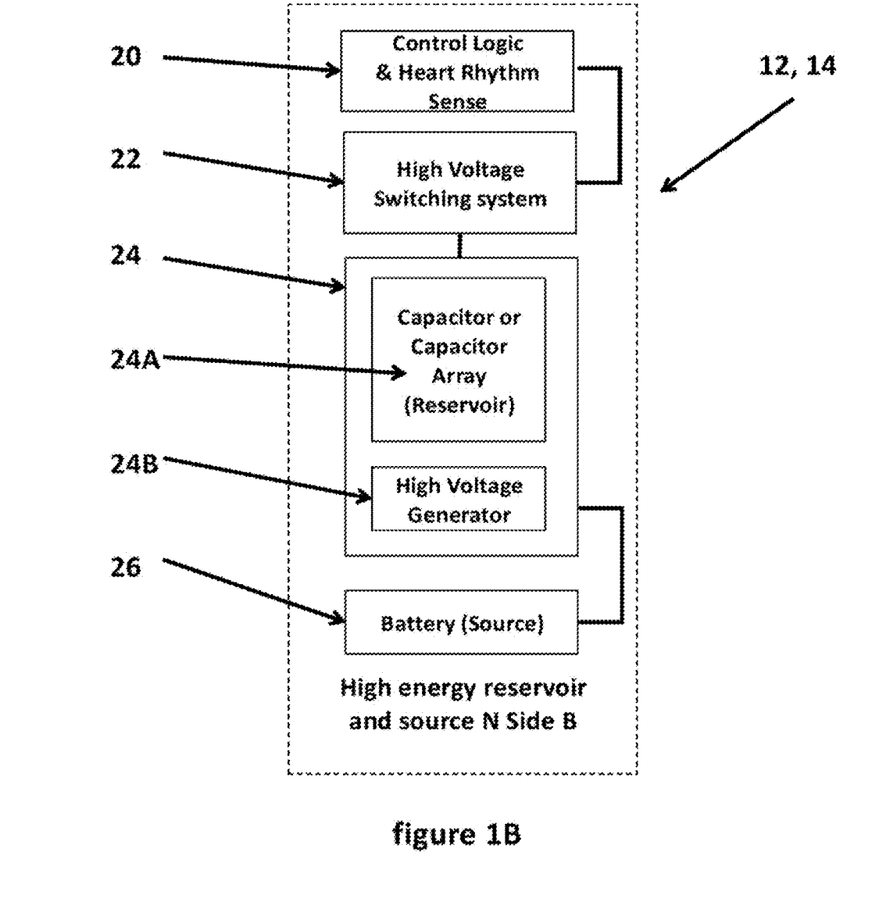

The multiphasic pulse system overcomes the limitation on the amplitude of follow on phases of the pulse waveform by using two or more high-energy reservoirs and/or sources, such as the four shown in FIGS. 1A and 1B. The pulse system 10 is not limited to any particular number of energy reservoirs (such as capacitors) or energy sources (such as batteries). The pulse system 10 may have a plurality or "n" number (as many as wanted) subsystems 12, 14 that together can be utilized to provide the various multiphasic waveforms, examples of which are shown in FIGS. 5-9 and described below. In the example implementation shown in FIG. 1A, there may be two sides, such as side A and side B as shown, and each side may have one or more of the subsystems 12, 14 and each subsystem may generate a pulse (that may be a positive pulse or a negative pulse.) The two or more subsystems 12, 14 permit the system to shape the various characteristics of a positive phase of the waveform separately from the shaping of the characteristics of the negative phase of the waveform and vice versa. The above described functions may be accomplished through the use of a fast switching high-energy/voltage switch system as described below.

Figure 4:
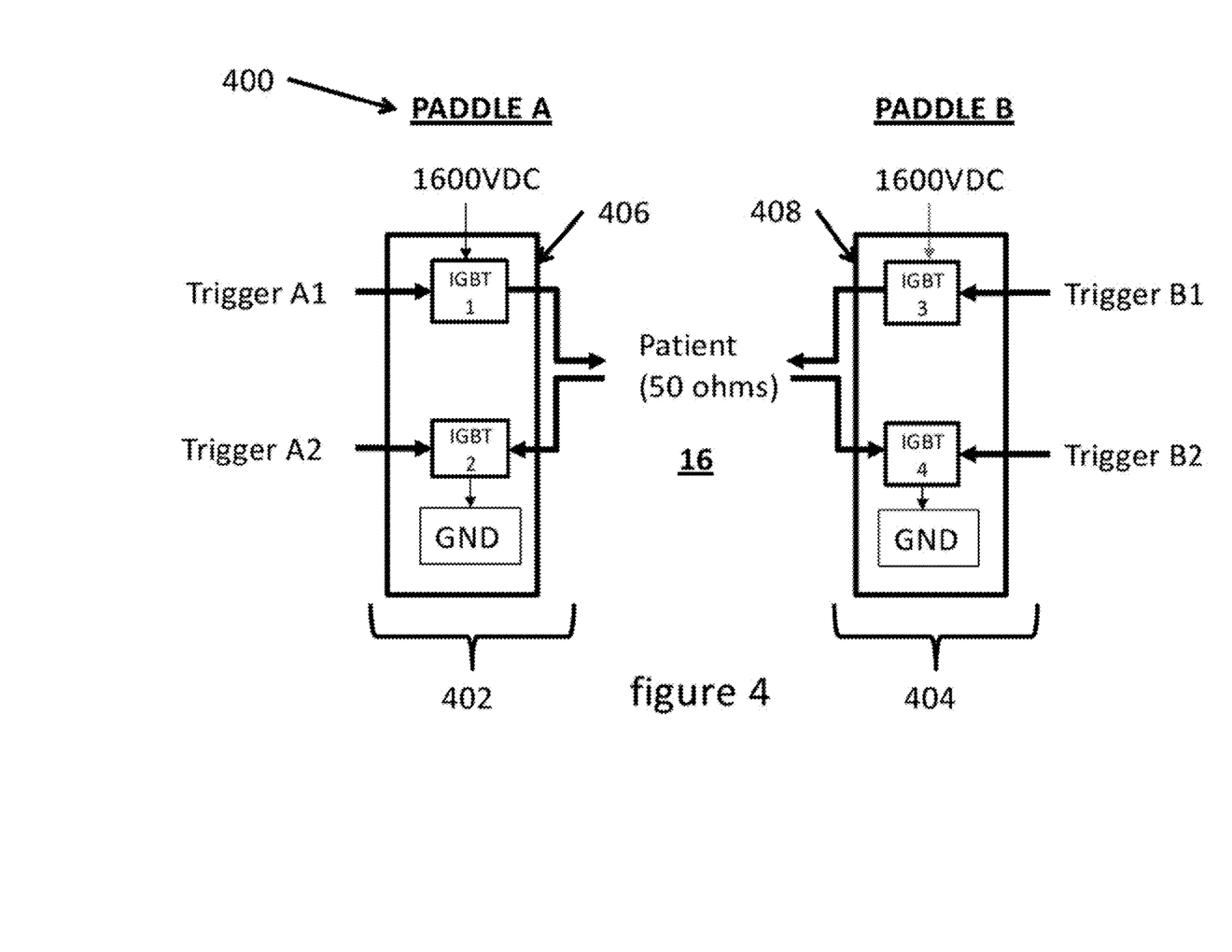
FIG. 4 illustrates an H-bridge circuit in the multiphasic waveform system.

Each subsystem 12, 14 of each side, as shown in FIG. 1B, may have a control logic and heart rhythm sense component 20 (that is connected to a similar component on the other side by a digital control link 30 as shown in FIG. 1A) that may be also coupled to a high voltage switching system component 22. The high voltage switching system component 22 may be implemented using either analog circuits or digital circuits or even some hybrid of the two approaches. Furthermore, the high voltage switching system component 22 may be implemented through the use of mechanical or solid-state switches or a combination of the two. As shown in FIG. 4, the high voltage switching system component 22 may be implemented using one or more semiconductor circuits, such as the insulated gate bipolar transistors. The high voltage switching system component 22 may be coupled to an energy reservoir 24 and the energy reservoir 24 may be coupled to a power source 26, such as a battery. The energy reservoir 24 may further comprise a reservoir 24A, such as for example one or more capacitors or a capacitor array, and a high voltage generator 24B. The energy reservoir 24 may also be coupled, by a high voltage return line 32 to the other side of the system as shown in FIG. 1A. The high voltage return 32 electrically completes the circuit and is present in existing defibrillators, but in a slightly different form since in the existing style of devices it is split into two parts: in the form of the two leads which go from the main defibrillator device to the internal or external surface of the patient.

The control logic and heart rhythm sense component 20 is well known in the art and the component analyzes the ECG signals from the patient for treatable arrhythmias and then chooses to shock the patient when a treatable arrhythmia is detected, along with guiding the operator through both visual and audible means through this process when the device is of the external automated variety. The control logic and heart rhythm sense component 20 also may control and shape the therapeutic pulse as it is delivered from the energy reservoir and ensures that it is as optimal as possible for the individual patient. In the implementations shown in FIGS. 1A and 2, the control logic and heart rhythm sense component 20 may generate the therapeutic pulse using the one or more groups of subsystems since each subsystem may have its own control logic 20 (so that each of them can control just the portion/phase of the pulse/waveform that they deliver. This provides a much higher level of control over what range of waveform shapes can be used/delivered, including many that are not possible with the existing devices. This also provides better weight and size distribution, as well as size and weight reductions, and the ability to have the devices look radically different and be handled in very different ways—ones that are much more operator intuitive. The disclosed system also provides a much higher level of redundancy and fault mitigation for the device embodiments that use it.

In one implementation, each control logic in each subsystem may have a circuit that can be used to adjust the shape of each portion of the therapeutic pulse. The circuit, may be for example, an array of resistors of various strengths and switches so that one or more of the resistor may be selected (as an array of selectable resistors) that can optimize and alter an RC constant of a subsystem's pulse phase generating circuitry in order to dynamically shape one or more pulse phases.

Figure 2:
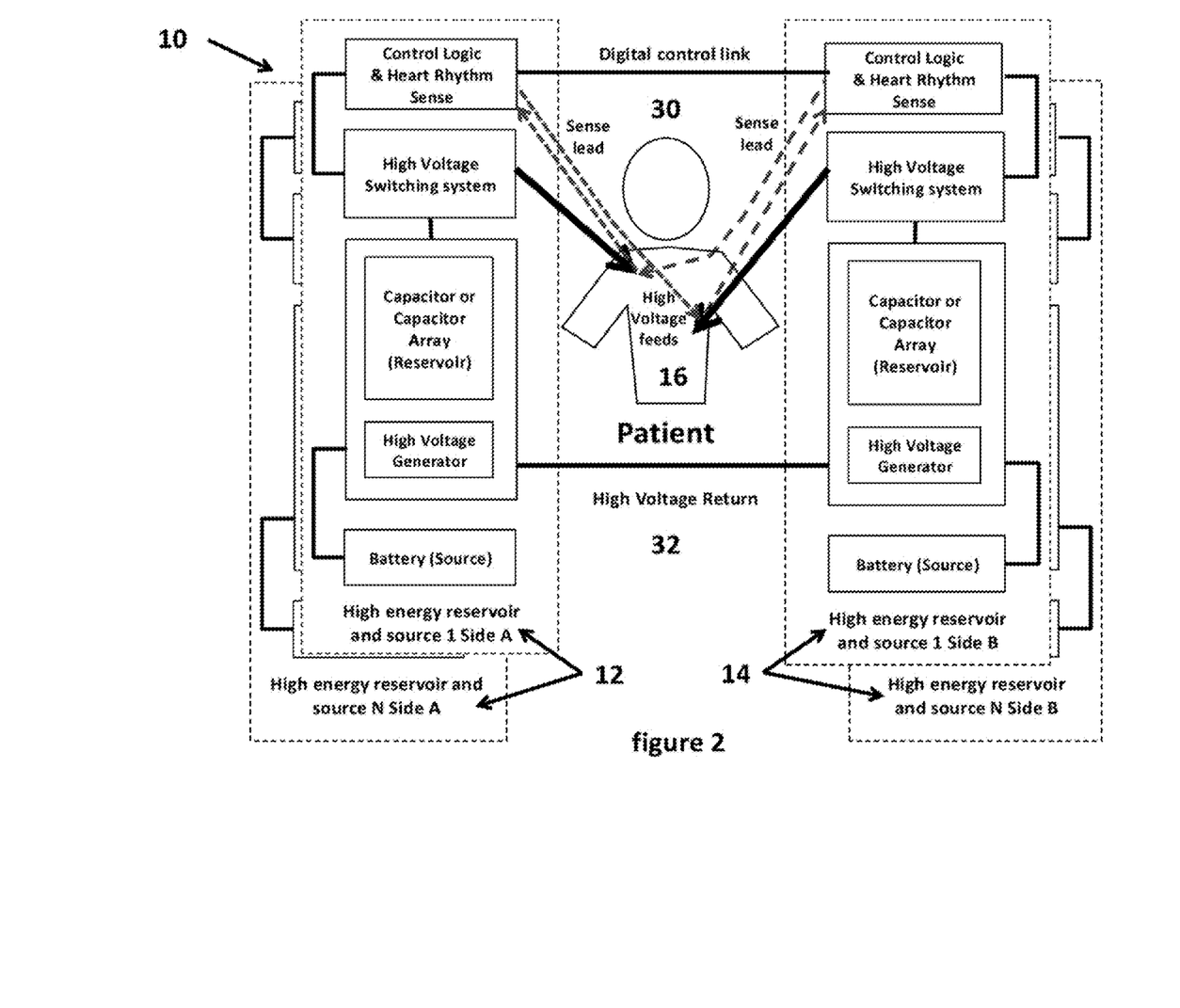
FIG. 2 illustrates another embodiment of the multiphasic waveform system with two independent subsystems each with its own energy reservoir and energy source.
Figure 9:
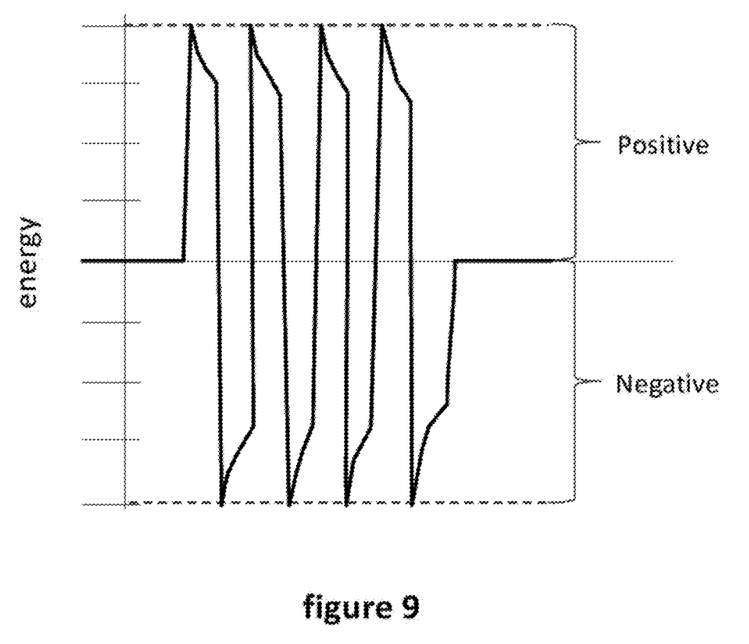
FIG. 9 illustrates a shape of Multiphasic pulse waveform that may be generated by the systems in FIGS. 1 and 2 where the negative phases of the waveform are interlaced or alternated with those of the positive phases of the waveform, where the amplitudes of each phase remain the same.

In some embodiments of the system, the system may provide for the recharging of individual energy reservoirs by the energy sources during times (including inter-pulse times) that an individual energy reservoir is not selected for discharge as shown in FIGS. 1A and 2. This provides the opportunity to interlace equivalent amplitude initial multiphasic pulses utilizing several different high energy reservoirs as shown in FIG. 9.

In one implementation, the system 10 may consist of two or more high-energy therapeutic pulse delivery sub-systems 12, 14 as shown in FIG. 2, such as Side A and Side B. In the implementation shown in FIG. 2, the side A may deliver one or more of a Positive phase waveform of the Multiphasic therapeutic pulse and Side B may deliver one or more of a Negative phase waveform of the Multiphasic therapeutic pulse. The subsystem in each side of the system in FIG. 2 may have the same elements as shown in FIG. 1B and described above. As shown in FIGS. 1A and 2, the subsystems may be coupled to the patient 16 by one or more high voltage leads and one or more sense leads wherein the high voltage leads deliver the therapeutic pulse and the sense leads are used to detect the heartbeat by the control unit.

The system 10 may either be pre-programmed to use a specific single multiphasic pulse shape, according to which one is shown to be most efficacious in clinical lab testing/trials, or else it may select the best one for a given purpose from a lookup table where they are listed according to their suitability for optimally resolving different types of arrhythmia that are being screened for and identified or for the different treatments as described above. Regardless, the system and method allows the use and application of a much wider range of pulse shapes than has been previously possible and this will allow the devices which use this invention to keep up with clinical developments as waveforms continue to be improved.

FIG. 3 illustrates a typical H-bridge circuit 300 and FIG. 4 illustrates an H-bridge circuit concept used in the multiphasic waveform system. As shown in FIG. 3, an H-bridge circuit is a known electronic circuit that enables a voltage, such as Vin, to be applied across a load, M, in either direction using one or more switches (S1-S4) (see http://cp.literature.agilent.com/litweb/pdf/5989-6288EN.pdf that is incorporated by reference herein for additional details about the H-bridge circuit.) As shown in FIG. 3, the H-bridge circuit may have a first portion 302 and a second portion 304 that form the complete H-bridge circuit.

As shown in FIG. 4, the H-bridge circuit may be part of the control circuits or switching systems shown in FIGS. 1-2. The load of the H-bridge circuit in the multiphasic system is the patient 16 to which the therapeutic pulse is going to be applied to provide treatment to the patient. The treatment to the patient, depending on the power and/or energy level of the therapeutic pulse may be for cardiac pacing, cardioversion, defibrillation, neurological therapy, nerve therapy or musculoskeletal therapy. Each side of the multiphasic system may generate its energy as described above and an H-bridge circuit 400 may be used to apply two (or more) unique energy sources to the single load. In the example shown in FIG. 4, each side of the system (such as side A and side B shown in FIGS. 1A and 2) may have a portion 402, 404 of the H-bridge so that the multiphasic system has a complete H-bridge circuit that is combination of portions 402, 404. The multiphasic system may then be used to deliver the therapeutic pulse through defibrillation paddles, such as Paddle A and Paddle B as shown in FIG. 4) to the patient.

Each portion 402, 404 of the H-bridge has its own energy source, 1600 VDC in the example in FIG. 4. In each portion of the H-bridge, the energy source may be switched using switches 406, 408 to make contact with the patient at a separate but specific time. The switches for each portion may be part of the switching system shown in FIGS. 1-2. In the example in FIG. 4, each portion may have two switches and each switch may be a commercially available insulated-gate bipolar transistor (IGBT.) Each switch may be controlled by a separate trigger signal as shown to discharge the energy to the patient. This provides for the two or more energy sources to discharge their energy to the load (patient) at a precise time, generating a resulting Biphasic discharge pulse or other therapeutic pulse shapes (examples of which are shown in FIGS. 5-9) as defined for an application, or therapeutic condition.

Figure 5:
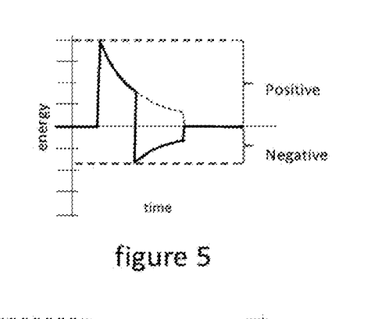
FIG. 5 illustrates a Biphasic pulse waveform where the negative phase of the waveform is smaller in amplitude than that of the positive phase of the waveform.
Figure 6:
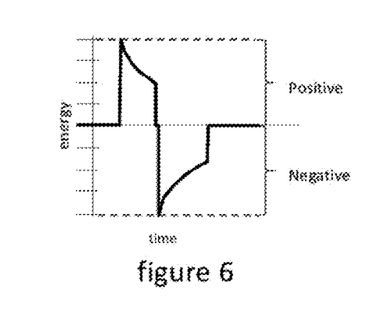
FIG. 6 illustrates a shape of a Biphasic pulse waveform that may be generated by the systems in FIGS. 1 and 2 where the negative phase of the waveform is identical in amplitude to that of the positive phase of the waveform.
Figure 7:
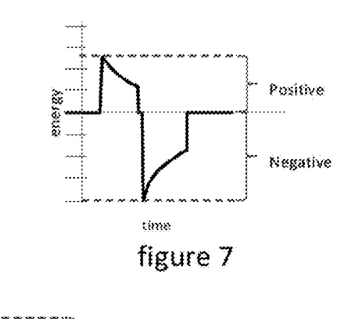
FIG. 7 illustrates a shape of Biphasic pulse waveform that may be generated by the systems in FIGS. 1 and 2 where the negative phase of the waveform is larger in amplitude to that of the positive phase of the waveform.
Figure 8:
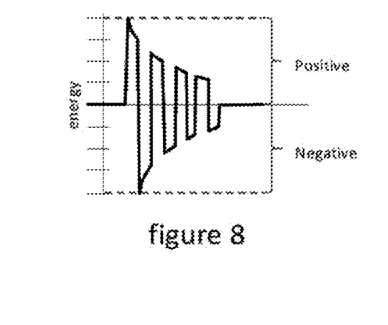
FIG. 8 illustrates a shape of Multiphasic pulse waveform that may be generated by the systems in FIGS. 1 and 2 where the negative phases of the waveform are interlaced or alternated with those of the positive phases of the waveform, where the amplitudes of each phase steadily decrease.

In the system, a therapeutic pulse may comprise one or more positive pulses and one or more negative pulses. As shown in FIGS. 1A and 2, each side (A & B) has one or more independent high-energy subsystems 12, 14 so that the magnitude and the timing for each of the Positive & Negative phases of the Multiphasic therapeutic pulse are independent and can therefore be independently controlled so as to provide a variety of different pulses as shown in FIGS. 5-9. FIG. 5 is typical of the current Biphasic therapeutic pulses available in many defibrillators currently on the market today (with a positive pulse and negative pulse as shown) that may also be generated by the systems in FIGS. 1A and 2. FIG. 6 illustrates a therapeutic pulse generated by the pulse system in which the magnitude of the Positive and Negative phases of the waveform are equal in starting amplitude. Furthermore, because each side or portion of the waveform generating circuit (subsystems A & B) are independent, the amplitude of the Positive phase of the waveform can be smaller in magnitude than the Negative phase of the waveform, as illustrated in FIG. 7. Additionally, due to the independent nature of the two (or more) subsystems in the circuit, it is possible to alternate the Positive and Negative phases at intervals throughout the delivery of the Multiphasic therapeutic pulse as shown in FIGS. 8 and 9, or that the second (or later) phase of the pulse can be of a measurably lower amplitude than would normally be deliverable from a single partially depleted energy reservoir. Further, each of the subsystems may have a dynamically variable and selectable voltage output such that the amplitude of each pulse phase can be individually controlled. In one implementation of the system, the therapeutic pulses in FIGS. 4-9 may be therapeutic defibrillation or cardioversion pulses. In another implementation of the system, the therapeutic pulses in FIGS. 5-9 may be lower energy therapeutic pulses used in the treatment of neurological, nerve or musculoskeletal conditions. Thus, the pulse generation system may generate pulse phases at any of a variety of power and energy levels allowing for the use of the pulses for a variety of purposes such as in cardiac pacing, cardioversion and defibrillation in addition to neurological, nerve or musculoskeletal therapies.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A multiphasic pulse generator, comprising:
   at least a first subsystem that generates a first phase of a pulse, the first subsystem having a power source and an energy reservoir, wherein the first phase is one of a positive phase of the pulse and a negative phase of the pulse;
   at least a second subsystem that generates a second phase of the pulse, the second subsystem having a second power source and a second energy reservoir, wherein the second phase is an opposite polarity phase to the first phase; and a switching component that switches between the first and second subsystems to generate a therapeutic pulse having at least one positive phase and at least one negative phase.

2. The generator of claim 1 further comprising a first circuit that adjusts a shape of the first phase of the pulse.

3. The generator of claim 2 further comprising a second circuit that adjusts a shape of the second phase of the pulse.

4. The generator of claim 2, wherein the first circuit includes an array of selectable resistors.

5. The generator of claim 3, wherein the second circuit includes an array of selectable resistors.

6. The generator of claim 1, wherein the therapeutic pulse is one out of a plurality of different possible power and energy levels suitable for use in one of cardiac pacing, cardioversion, defibrillation, neurological therapies, nerve therapies and musculoskeletal therapies.

7. The generator of claim 1 further comprising a circuit to individually select an amplitude of one or more of the first phase of the pulse and second phase of the pulse.

8. The generator of claim 1, wherein the at least first subsystem has a control circuit and the at least second subsystem has a control circuit.

9. A multiphasic pulse generator, comprising:
at least a first subsystem that generates a first phase of a pulse, the first subsystem having a power source, an energy reservoir and a portion of an H-bridge circuit, wherein the first phase is one of a positive phase of the pulse and a negative phase of the pulse;
at least a second subsystem that generates a second phase of the pulse, the second subsystem having a second power source, a second energy reservoir and a second portion of the H-bridge circuit so that a complete H-bridge circuit is formed between the at least first and second subsystems, wherein the second phase is an opposite polarity phase to the first phase; and
a switching component that switches between the first and second subsystems to generate a therapeutic pulse having at least one positive phase and at least one negative phase.

10. The generator of claim 9 further comprising a first circuit that adjusts a shape of the first phase of the pulse.

11. The generator of claim 10 further comprising a second circuit that adjusts a shape of the second phase of the pulse.

12. The generator of claim 10, wherein the first circuit includes an array of selectable resistors.

13. The generator of claim 11, wherein the second circuit includes an array of selectable resistors.

14. The generator of claim 9, wherein the therapeutic pulse is one out of a plurality of different possible power and energy levels suitable for use in one of cardiac pacing, cardioversion, defibrillation, neurological therapies, nerve therapies and musculoskeletal therapies.

15. The generator of claim 9 further comprising a circuit to individually select an amplitude of one or more of the first phase of the pulse and second phase of the pulse.

16. The generator of claim 9, wherein the at least first subsystem has a control circuit and the at least second subsystem has a control circuit.

17. A method for generating a therapeutic pulse, comprising:
generating one or more positive phases for a pulse using a power source and an energy reservoir;
generating one or more negative phases for a pulse using a second power source and a second energy reservoir; and
switching between the one or more positive phases and the one or more negative phases to generate a therapeutic pulse having at least one positive phase and at least one negative phase;
wherein the power source, the energy reservoir, the second power source, and the second energy reservoir are housed in a multiphasic pulse generator.

18. The method of claim 17 further comprising adjusting a shape of each of the one or more positive phases.

19. The method of claim 18 further comprising adjusting a shape of each of the one or more negative phases.

20. The method of claim 17, wherein generating the therapeutic pulse further comprises generating a therapeutic pulse having a plurality of different possible power and energy levels suitable for use in one of cardiac pacing, cardioversion, defibrillation, neurological therapies, nerve therapies and musculoskeletal therapies.

21. The method of claim 17 further comprising individually selecting an amplitude of one or more of the one or more positive phases and one or more negative phases of the pulse.

* * * * *